United States Patent
Spangler et al.

(10) Patent No.: US 11,413,063 B2
(45) Date of Patent: Aug. 16, 2022

(54) ATHERECTOMY SYSTEM WITH GUIDEWIRE DETECTION

(71) Applicant: BOSTON SCIENTIFIC SCIMED, INC., Maple Grove, MN (US)

(72) Inventors: David Gordon Spangler, New Richmond, WI (US); Corydon Carlson, Stillwater, MN (US); Laszlo Trent Farago, Hudson, WI (US); Daniel Frank Massimini, Brooklyn Park, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 338 days.

(21) Appl. No.: 16/444,761

(22) Filed: Jun. 18, 2019

(65) Prior Publication Data

US 2020/0397463 A1    Dec. 24, 2020

(51) Int. Cl.
*A61B 17/3207* (2006.01)
*A61B 17/22* (2006.01)
(Continued)

(52) U.S. Cl.
CPC ...... *A61B 17/320758* (2013.01); *A61B 17/22* (2013.01); *A61M 25/09* (2013.01); *A61B 2017/00199* (2013.01); *A61B 2017/22038* (2013.01); *A61B 2017/22094* (2013.01); *A61B 2017/320741* (2013.01); *A61F 2/01* (2013.01)

(58) Field of Classification Search
CPC ............ A61B 17/320758; A61B 17/22; A61B 2017/00199; A61B 2017/22038; A61B 2017/22094; A61B 2017/320741; A61B 2017/22049; A61B 2017/00075; A61B 2017/00119; A61B 2017/00017; A61B 2017/00398; A61B 2090/066; A61B 2090/08021; A61M 25/09; A61M 25/09041; A61F 2/01
See application file for complete search history.

(56) References Cited

U.S. PATENT DOCUMENTS 5,709,661 A    1/1998   Van Egmond et al.
6,106,301 A *  8/2000   Merril ................. G09B 23/285
                                                    434/262
(Continued)

FOREIGN PATENT DOCUMENTS

IE    S2009529 A2    4/2012
WO   2020055728 A1   3/2020

OTHER PUBLICATIONS

International Search Report and Written Opinion dated Sep. 4, 2020 for International Application No. PCT/US2020/038132.

*Primary Examiner* — Richard G Louis
*Assistant Examiner* — Chima U Igboko
(74) *Attorney, Agent, or Firm* — Seager, Tufte & Wickhem, LLP (57) ABSTRACT

An atherectomy system includes a drive mechanism adapted to rotatably actuate an atherectomy burr and a controller that is adapted to regulate operation of the drive mechanism. A guidewire motion detector is adapted to detect movement of the guidewire. The controller is further adapted to take action when the guidewire motion detector detects movement of the guidewire relative to the drive mechanism while the drive mechanism is operating.

16 Claims, 12 Drawing Sheets

(51) Int. Cl.
*A61M 25/09* (2006.01)
*A61B 17/00* (2006.01)
*A61F 2/01* (2006.01)

(56) References Cited

U.S. PATENT DOCUMENTS

| | | | |
|---|---|---|---|
| 6,113,615 A * | 9/2000 | Wulfman | A61B 17/320758 606/159 |
| 2005/0004579 A1 | 1/2005 | Schneider et al. | |
| 2012/0179167 A1 * | 7/2012 | Wenderow | A61B 34/30 606/130 |
| 2013/0274657 A1 * | 10/2013 | Zirps | A61M 25/0147 604/95.01 |
| 2014/0261453 A1 * | 9/2014 | Carlson | A61M 25/09041 128/849 |
| 2014/0316448 A1 | 10/2014 | Higgins | |
| 2015/0011834 A1 * | 1/2015 | Ayala | A61B 17/0218 29/428 |
| 2015/0173838 A1 * | 6/2015 | Murphy | A61B 34/30 606/130 |

\* cited by examiner

ATHERECTOMY SYSTEM WITH GUIDEWIRE DETECTION

TECHNICAL FIELD

The present disclosure pertains to medical devices, and methods for manufacturing and using medical devices. More particularly, the disclosure is directed to devices and methods for removing occlusive material from a body lumen. Further, the disclosure is directed to an atherectomy device for forming a passageway through an occlusion of a body lumen, such as a blood vessel.

BACKGROUND

Many patients suffer from occluded arteries and other blood vessels which restrict blood flow. Occlusions can be partial occlusions that reduce blood flow through the occluded portion of a blood vessel or total occlusions (e.g., chronic total occlusions) that substantially block blood flow through the occluded blood vessel. In some cases a stent may be placed in the area of a treated occlusion. However, restenosis may occur in the stent, further occluding the vessel and restricting blood flow. Revascularization techniques include using a variety of devices to pass through the occlusion to create or enlarge an opening through the occlusion. Atherectomy is one technique in which a catheter having a cutting element thereon is advanced through the occlusion to form or enlarge a pathway through the occlusion. A need remains for alternative atherectomy devices to facilitate crossing an occlusion.

SUMMARY

This disclosure provides design, material, manufacturing method, and use alternatives for medical devices. For example, an atherectomy system includes an atherectomy burr and a drive mechanism that is adapted to rotatably actuate the atherectomy burr as well as to accommodate a guidewire extending therethrough. A guidewire extends through the drive mechanism. A guidewire motion detector is adapted to detect movement of the guidewire. A controller is operably coupled to the guidewire motion detector and is adapted to regulate operation of the drive mechanism. The controller is further adapted to take action when the guidewire motion detector detects movement of the guidewire relative to the drive mechanism while the drive mechanism is operating.

Alternatively or additionally, the controller may be further adapted to cease operation of the drive mechanism when the guidewire motion detector detects movement of the guidewire.

Alternatively or additionally, the controller may be further adapted to provide an alarm when the guidewire motion detector detects movement of the guidewire.

Alternatively or additionally, the guidewire motion detector may be further adapted to determine whether the guidewire is present within the drive mechanism.

Alternatively or additionally, the guidewire motion detector may include an optical detector adapted to permit the guidewire to pass through the optical detector, wherein the presence of the guidewire is detected by the guidewire blocking at least some of the light passing through the optical detector.

Alternatively or additionally, the guidewire motion detector may include an axial encoding wheel positioned in contact with the guidewire such that translation of the guidewire causes the axial encoding wheel to rotate.

Alternatively or additionally, the guidewire motion detector may further include a position sensing encoder that is positioned to detect rotation of the axial encoding wheel and send an axial motion signal to the controller.

Alternatively or additionally, the axial encoding wheel may include a plurality of slots extending through the axial encoding wheel and the guidewire motion detector further comprises an optical sensor sensitive to changes in light passing through the plurality of slots extending through the axial encoding wheel.

Alternatively or additionally, the guidewire motion detector may include a radial encoding wheel positioned in contact with the guidewire such that rotation of the guidewire causes the radial encoding wheel to rotate.

Alternatively or additionally, the guidewire motion detector may further include a position sensing encoder that is positioned to detect rotation of the radial encoding wheel and send a radial motion signal to the controller.

Alternatively or additionally, the radial encoding wheel may include a plurality of slots extending through the radial encoding wheel and the guidewire motion detector further comprises an optical sensor sensitive to changes in light passing through the plurality of slots extending through the radial encoding wheel.

Alternatively or additionally, the guidewire motion detector may include a track ball positioned to contact the guidewire such that translation or rotation of the guidewire causes the track ball to move, a light source positioned such that light from the light source impinges on the track ball and a light detector positioned such that light reflected from the track ball contacts the light detector, wherein changes in the light detected by the light detector indicates movement of the track ball and thus indicates movement of the guidewire.

Alternatively or additionally, the guidewire motion detector may include a light source positioned such that light from the light source impinges on the guidewire and a light detector positioned such that light reflected from the guidewire contacts the light detector, wherein changes in the light detected by the light detector indicates movement of the guidewire.

Alternatively or additionally, the atherectomy system may further include a wire brake that facilitates insertion of the guidewire into the drive mechanism, the guidewire motion detector secured relative to the wire brake.

Alternatively or additionally, the drive mechanism may include a drive cable coupled with the atherectomy burr and a drive motor adapted to rotate the drive cable.

As another example, an atherectomy system includes an atherectomy burr and a drive mechanism that is adapted to rotatably actuate the atherectomy burr as well as to accommodate a guidewire extending therethrough. A guidewire extends through the drive mechanism. A first encoding wheel is positioned in contact with the guidewire such that translation of the guidewire relative to the drive mechanism causes the first encoding wheel to rotate. A first position sensor is adapted to detect rotation of the first encoding wheel and to output a translation movement signal. A second encoding wheel is positioned in contact with the guidewire such that rotation of the guidewire relative to the drive mechanism causes the second encoding wheel to rotate. A second position sensor is adapted to detect rotation of the second encoding wheel and to output a rotation movement signal. A controller is operably coupled to the guidewire motion detector and is adapted to regulate operation of the drive mechanism, and is further adapted to receive the translation movement signal and/or the rotation movement signal and to take action when either the translation movement signal or the rotation movement signal indicates guidewire movement relative to the drive mechanism.

Alternatively or additionally, taking action may include at least one of ceasing operating of the drive mechanism and providing an alarm.

Alternatively or additionally, the drive mechanism may include a drive cable coupled with the atherectomy burr and a drive cable that is adapted to rotate the drive cable.

In another example, an atherectomy system includes an atherectomy burr and a drive mechanism that is adapted to rotatably actuate the atherectomy burr as well as to accommodate a guidewire extending therethrough. A guidewire extends through the drive mechanism. A track ball is positioned to contact the guidewire such that translation or rotation of the guidewire causes the track ball to move. A light source is positioned such that light from the light source impinges on the track ball and a light detector is positioned such that light reflected from the track ball contacts the light detector, and changes in the light detected by the light detector causes the light detector to output a signal. A controller is operably coupled to the guidewire motion detector and is adapted to regulate operation of the drive mechanism, and is further adapted to receive the signal from the light detector and to take action when the signal from the light detector indicates movement of the guidewire relative to the drive mechanism while the drive mechanism is operating.

Alternatively or additionally, the drive mechanism may include a drive cable coupled with the atherectomy burr and a drive cable that is adapted to rotate the drive cable.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification. All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Many patients suffer from occluded arteries, other blood vessels, and/or occluded ducts or other body lumens which may restrict bodily fluid (e.g. blood, bile, etc.) flow. Occlusions can be partial occlusions that reduce blood flow through the occluded portion of a blood vessel or total occlusions (e.g., chronic total occlusions) that substantially block blood flow through the occluded blood vessel. Revascularization techniques include using a variety of devices to pass through the occlusion to create or enlarge an opening through the occlusion. Atherectomy is one technique in which a catheter having a cutting element thereon is advanced through the occlusion to form or enlarge a pathway through the occlusion. Ideally, the cutting element excises the occlusion without damaging the surrounding vessel wall and/or a previously implanted stent where restenosis has occurred. However, in some instances the cutting element may be manipulated and/or advanced such that it contacts the vessel wall and/or the stent. Therefore, it may be desirable to utilize materials and/or design an atherectomy device that can excise an occlusion without damaging the surrounding vessel and/or a previously implanted stent where restenosis has occurred. Additionally, it may be desirable that a cutting element be useful in removing hard occlusive material, such as calcified material, as well as softer occlusive material. The methods and systems disclosed herein may be designed to overcome at least some of the limitations of previous atherectomy devices while effectively excising occlusive material. For example, some of the devices and methods disclosed herein may include cutting elements with unique cutting surface geometries and/or designs.

Figure 1:
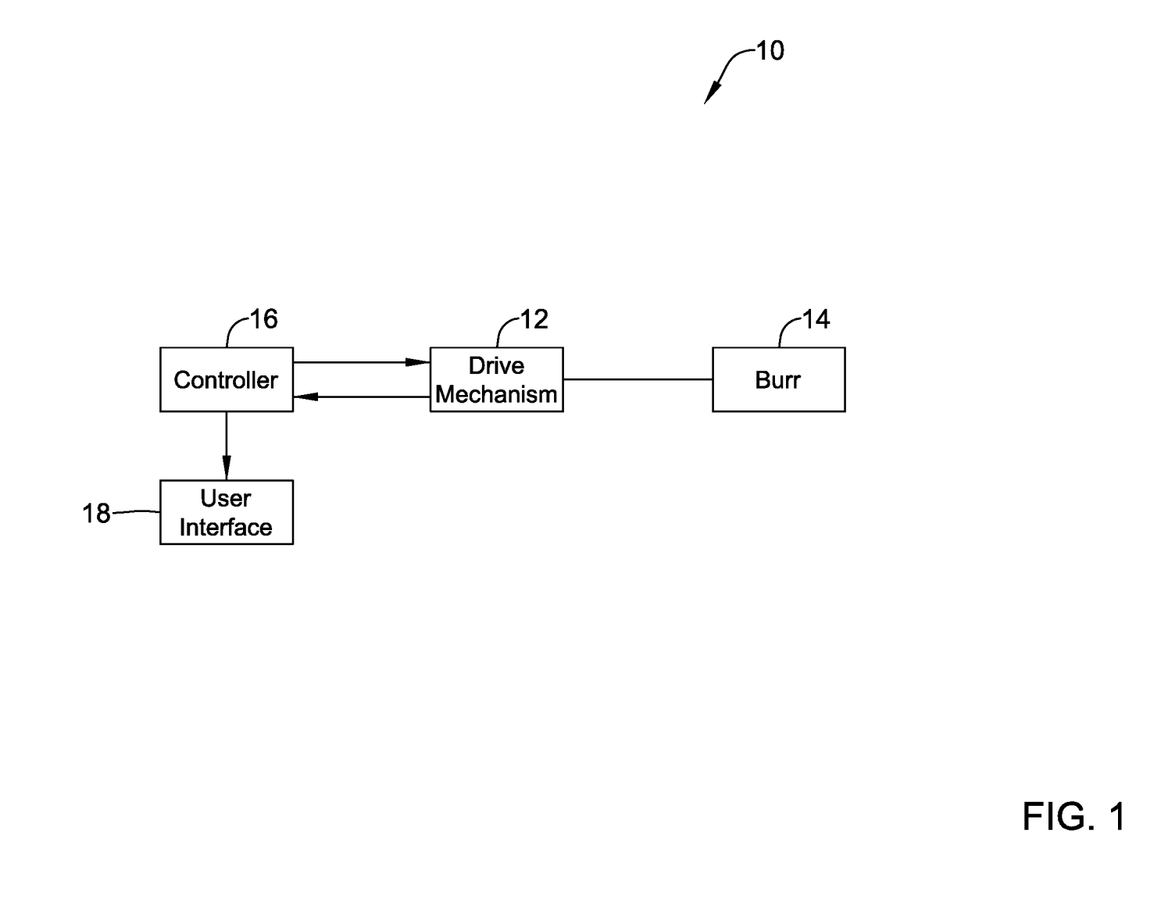
FIG. 1 is a schematic block diagram of an example atherectomy system.

FIG. 1 is a schematic block diagram of an example atherectomy system 10 that includes a drive mechanism 12 that is adapted to rotatably actuate an atherectomy burr 14. The atherectomy system 10 includes a controller 16 that is adapted to regulate operation of the drive mechanism 12. In some cases, the atherectomy system 10 may include a user interface 18 that may be operably coupled to the controller 16 such that the controller 16 is able to display information regarding the performance of the drive mechanism 12. This information may, for example, include one or more of an instantaneous speed of the drive mechanism 12, an instantaneous torque being experienced by the atherectomy burr 14, and the like. In some instances, the atherectomy system 10 may not include the user interface 18. In some cases, the atherectomy burr 14 may also be referred to as being or including a cutting head or a cutting member, and these terms may be used interchangeably.

Figure 2:
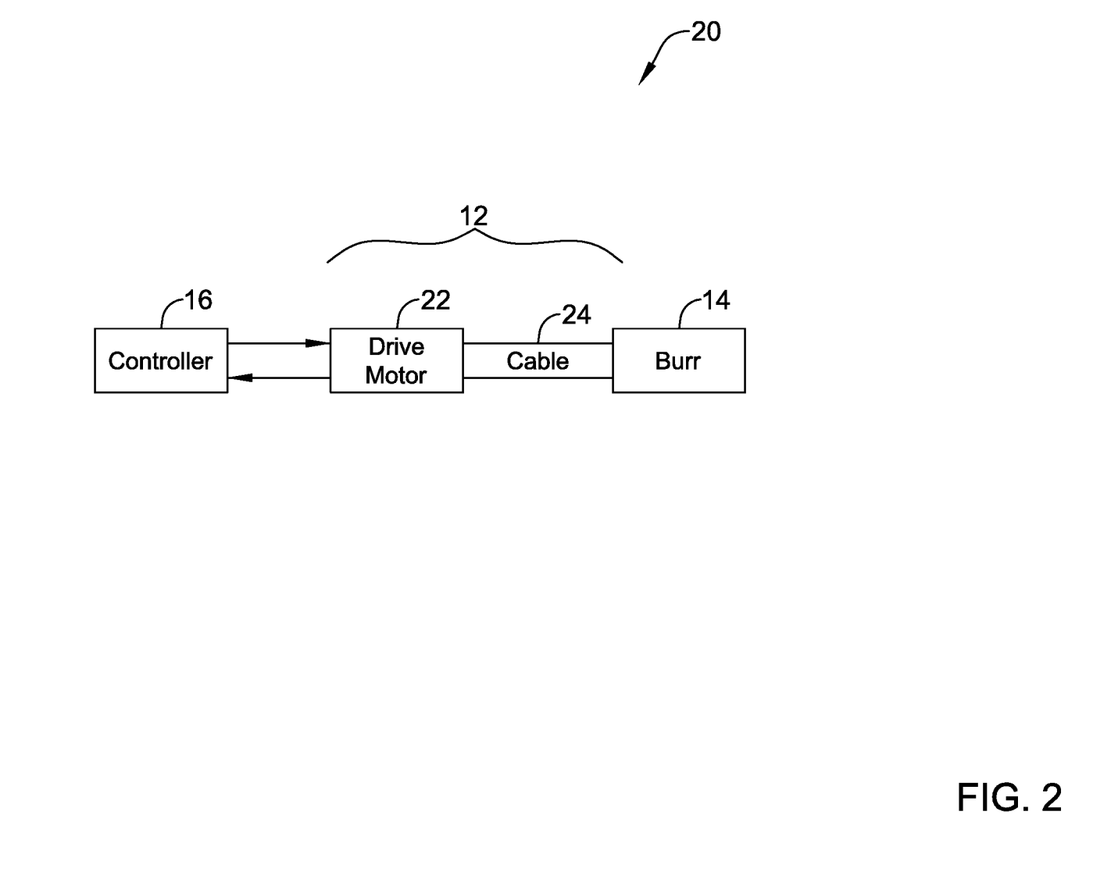
FIG. 2 is a schematic block diagram of an example atherectomy system.

FIG. 2 is a schematic block diagram of an example atherectomy system 20 in which the drive mechanism 12 may include a drive motor 22 and a drive cable 24 that is operably coupled with the drive motor 22 as well as the atherectomy burr 14. In some cases, features of the atherectomy system 20 may be combined with features of the atherectomy system 10. In some cases, the atherectomy system 20 may also include a handle (not shown).

Figure 3:
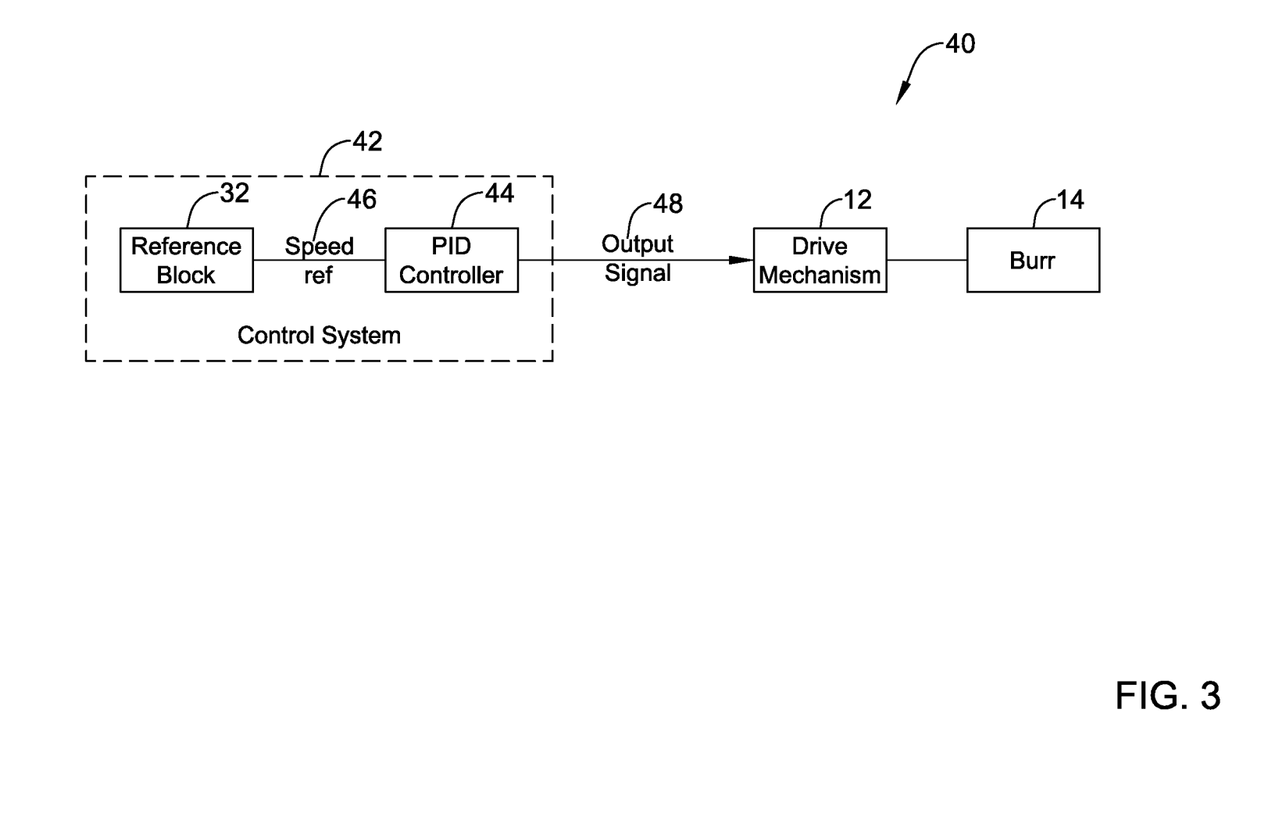
FIG. 3 is a schematic block diagram of an example atherectomy system.

FIG. 3 is a schematic block diagram of an example atherectomy system 40 that includes a control system 42 that is adapted to regulate operation of the drive mechanism 12 in order to rotatably actuate the atherectomy burr 14. In some cases, features of the atherectomy system 40 may be combined with one or more of the atherectomy system 10 and the atherectomy system 20. The control system 42 may include a reference block 32 as well as a Proportional Integral Derivative (PID) controller 44 that is operably coupled to the reference block 32. In some cases, the reference block 32 may determine a speed reference 46 that is selectable between a nominal value, a negative value and zero. In some instances, the PID controller 44 may be further adapted to add an offset value to the speed reference 46 received from the reference block 32, although in some cases, the reference block 32 may add the offset value. The PID controller 44 may be further adapted to provide a reduction in motor speed of the drive mechanism 12 that is greater than what would otherwise normally occur in response to an increasing torque experienced at the atherectomy burr 14.

Figure 4:
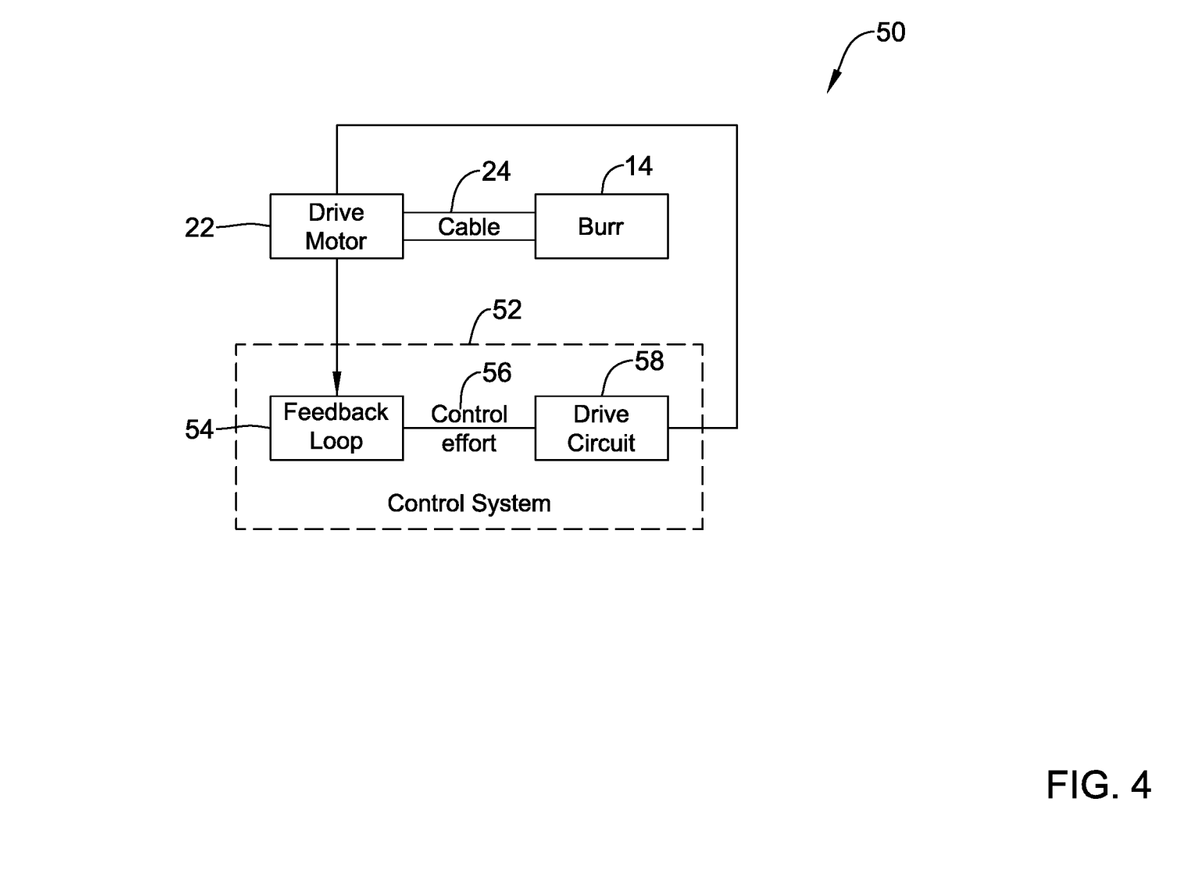
FIG. 4 is a schematic block diagram of an example atherectomy system.

FIG. 4 is a schematic block diagram of an example atherectomy system 50 that includes a control system 52 that is adapted to regulate operation of the drive motor 22 in order to rotatably actuate the atherectomy burr 14. In some cases, features of the atherectomy system 50 may be combined with one or more of the atherectomy system 10, the atherectomy system 20 or the atherectomy system 40. The control system 52 is operably coupled to the drive motor 22 and includes a feedback loop 54 that is adapted to monitor performance of the drive motor 22 and to output a control effort signal 56. A drive circuit 58 is adapted to receive the control effort signal 56 and to regulate operation of the drive motor 22 in accordance with the control effort signal 56.

In some cases, the feedback loop 54 may include a reference block for determining a speed reference and a Proportional Integral Derivative (PID) controller that is operably coupled to the reference block for receiving the speed reference, the PID controller adapted to utilize the speed reference, a Proportional (P) gain value, an Integral (I) gain value and a Derivative (D) gain value in determining the control effort signal. In some cases, the feedback loop 54 may be adapted to add an offset value to a reference signal provided to the reference loop 54 in order to accurately hold speed of the drive motor 22 during a no-load situation. In some instances, for example if the atherectomy burr 14 becomes stuck, the control system 52 may be further adapted to increase the torque provided by the drive motor 22 until a torque threshold is reached for a brief period of time, and to subsequently direct the drive motor 22 to reverse at a slow speed in order to unwind energy in the drive mechanism.

Figure 5:
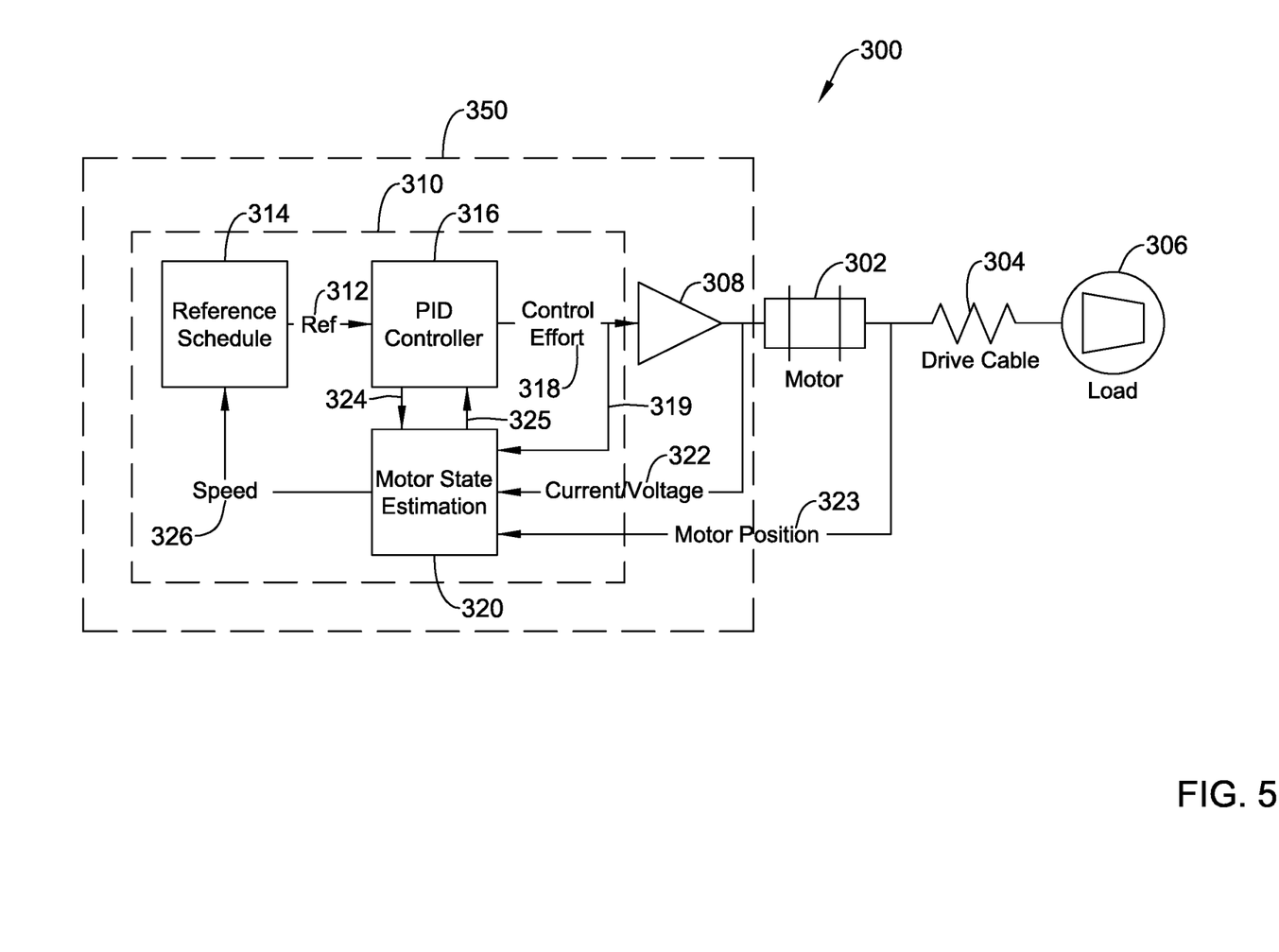
FIG. 5 is a schematic block diagram of an example atherectomy system.

FIG. 5 is a schematic block diagram of an example atherectomy system 300. In some cases, the atherectomy system 300 may be considered as being an example of the atherectomy system 10, 20, 40 or 50. In some instances, features of the atherectomy system 300 may be combined with features of any of the atherectomy systems 10, 20, 40 or 50, for example. The atherectomy system 300 includes a motor 302 that drives a drive cable 304 which itself engages a load 306. The load 306 represents an atherectomy burr, for example. The motor 302 is controlled by a drive circuitry 308 which may be considered as being an example of or otherwise incorporated into the drive motor 22 (FIG. 2) and/or the controller 16 (FIGS. 1-2), for example. In some cases, the motor 302 may be sized, relative to the weight and other dimensions of the atherectomy system 300, to be capable of accelerating the atherectomy burr to full speed in less than 3 seconds, or in some cases in less than 2 seconds. As an example, the motor 302 may be rated for at least 60 watts. In a particular example, the motor 302 may be rated for about 80 watts. These are just examples.

The drive circuitry 308 receives an input from a feedback portion 310. In some cases, the feedback portion 310 begins with a reference input 312 from a reference schedule block 314, which provides the reference input 312 to a PID controller 316. In some cases, the reference schedule block 314 may be configured to accept additional inputs, such as from a user and/or from additional sensors not illustrated. As an example, if the device has been running for too long of a period of time, the reference schedule block 314 may reduce the speed reference in order to prevent overheating. A PID controller is a controller that includes a (P) proportional portion, an (I) integral portion and a (D) derivative portion. The PID controller 316 outputs a control effort value or reference current 318 to the drive circuitry 308. A motor state estimation block 320 receives a current/voltage signal 322 and a motor position signal 323 from the drive circuitry 308 and receives state feedback 324 from the PID controller 316. The motor state estimation block 320 provides a state feedback signal 325 back to the PID controller 316.

The motor state estimation block 320 outputs a speed value 326 back to the reference schedule block 314. While the feedback from the motor state estimation block 320 to the reference schedule block 314 is shown as being a speed value, in some cases the feedback may additionally or alternatively include one or more of position, torque, voltage or current, and in some cases may include the derivative or integral of any of these values. In some cases, the motor state estimation block 320 may instead receive a signal 323 that represents speed, instead of position (as illustrated). The motor position signal 323 may be an indication of relative rotational position of an output shaft of the motor 302, and thus an indication of relative rotational position of the load 306, which if tracked over time may provide an indication of speed.

In some cases, the drive circuitry 308 and the feedback loop 310 may in combination be considered as forming a controller 350 that is adapted to determine an estimated torque at the atherectomy burr (the load 306 as shown in FIG. 5). The controller 350 may be considered as being an example of the controller 16 (FIG. 1). In some cases, the controller 350 may be considered as including only some elements of the drive circuitry 308 and the feedback loop 310. In some instances, some of the features and functions of the controller 350 may take place in the motor state estimation block 320. It will be appreciated that while FIG. 5 shows various components as standalone components, in some cases the functions of one or more of the components may actually be spread between separate components. In some instances, the functions of one or more of the components may be combined into one or more components.

If the estimated torque at the load 306 becomes too high, this may be an indication that the burr is getting stuck. In order to protect against possible damage to the drive cable 304, and to protect against possible injury to the patient, the atherectomy system 300 may be adapted to stop or even reverse operation of the atherectomy system 300 if the estimated torque meets or exceeds a predetermined torque threshold. It will be appreciated that the actual value of the predetermined torque threshold may vary, depending on the mechanics of the atherectomy system 300, but may be set at a level low enough to prevent damage and injury, but not set so low as to engender too many false alarms caused by minor and/or temporary torque increases that are not caused by the load 306 becoming stuck. For example, the instantaneous torque may vary by small amounts as the atherectomy system 300 progresses through the patient's vasculature.

Figure 6:
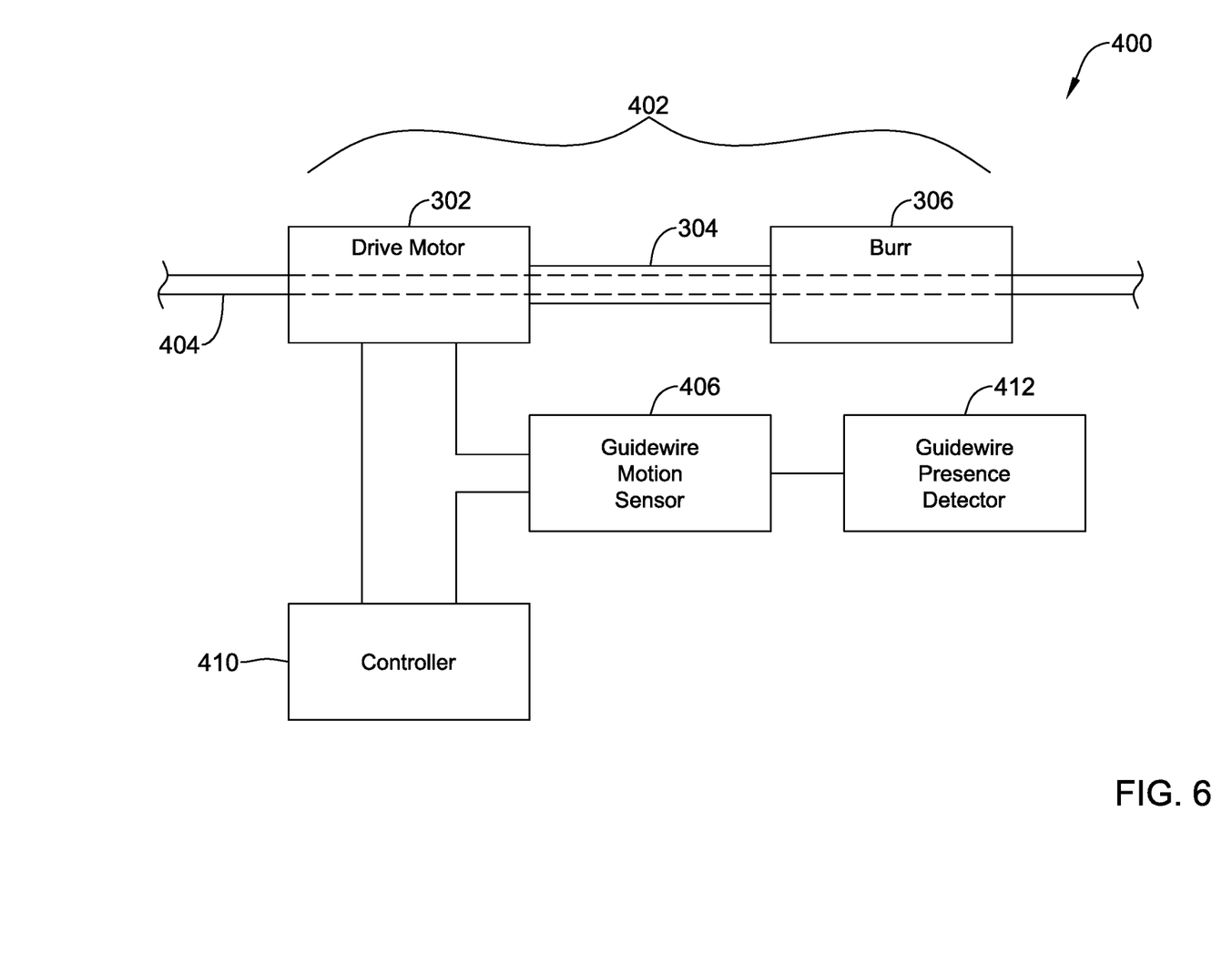
FIG. 6 is a schematic block diagram of an example atherectomy system.

FIG. 6 is a schematic block diagram of an example atherectomy system 400. In some cases, the atherectomy system 400 may be considered as being an example of the atherectomy system 10, 20, 40 or 50. In some instances, features of the atherectomy system 400 may be combined with features of any of the atherectomy systems 10, 20, 40 or 50, for example. The atherectomy system 400 includes a drive mechanism 402 that is adapted to rotatably actuate the atherectomy burr 306. In some instances, as shown, the drive mechanism 402 may be considered as including the drive motor 302 and the drive cable 304. While shown schematically, it will be appreciated that the drive mechanism 402 may be adapted to accommodate a guidewire 404 that extends through the drive mechanism 402 and through the atherectomy burr 306.

A guidewire motion detector 406 may be adapted to detect movement of the guidewire 404 relative to the drive mechanism 402. A controller 410, which may be considered as being an example of the controller 16 or the controller 350, is operably coupled to the guidewire motion detector 406 and is adapted to regulate operation of the drive mechanism 402. The controller 410 is adapted to take action when the guidewire motion detector 406 detects movement of the guidewire 404 relative to the drive mechanism 402. In some cases, taking action includes stopping operation of the drive mechanism 402. Taking action may additionally or alternatively include the controller 410 providing an alarm such as an auditory alarm, a visual alarm or a vibratory alarm so that the user understands that there may be a problem with securement of the guidewire 404.

In some cases, the guidewire motion detector 406 may be further adapted to determine whether the guidewire 404 is present within the drive mechanism 402. For example, the atherectomy system 400 may include (either as part of the guidewire motion detector 406 or as a separate component) a guidewire presence detector 412. The guidewire presence detector 412 may take any form. The guidewire presence detector 412 may, for example, be an optical device such as may otherwise be used to detect bubbles in a fluid. It will be appreciated that absent the guidewire 404, a certain amount of light will pass through a lumen adapted to accommodate the guidewire 404. With the guidewire 404 present, less light will pass through the aforementioned lumen. Accordingly, a light sensor may be used to detect the relative light level, and thus determine whether the guidewire 404 is present. This information may be communicated to the controller 410. When the guidewire 404 is not present, the controller 410 may alert the user, and/or may not permit operation of the drive mechanism 402.

Figure 7:
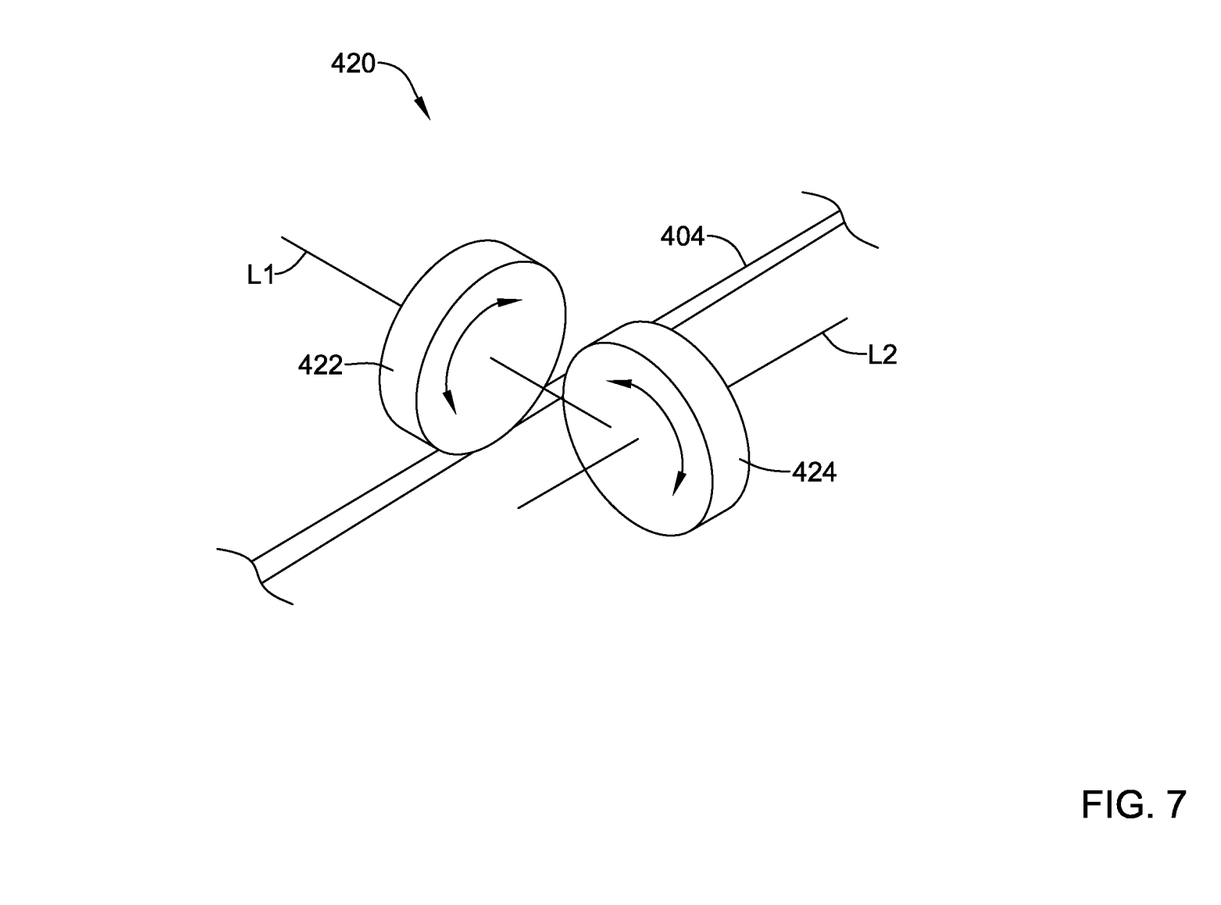
FIG. 7 is a schematic view of a guidewire motion detector usable in the example atherectomy system of FIG. 6.

FIG. 7 is a schematic view of a portion of a guidewire motion detector 420 that may be used as the guidewire motion detector 406 (FIG. 6). The guidewire motion detector 420 includes an axial encoding wheel 422 that is positioned in contact with the guidewire 404 and relative to the guidewire 404 such that translation, or axial movement, of the guidewire 404 will cause the axial encoding wheel to rotate about an axis L1. Similarly, the guidewire motion detector 420 includes a radial encoding wheel 424 that is positioned in contact with the guidewire 404 and relative to the guidewire 404 such that rotation of the guidewire 404 will cause the radial encoding wheel 424 to rotate about an axis L2. It will be appreciated that the axial encoding wheel 422 and the radial encoding wheel 424 are arranged such that the axis L1 is orthogonal to the axis L2. The axial encoding wheel 422 may be positioned above or below the guidewire 404, for example. The radial encoding wheel 424 may be positioned above, below, in front of or behind the guidewire 404.

Figure 8:
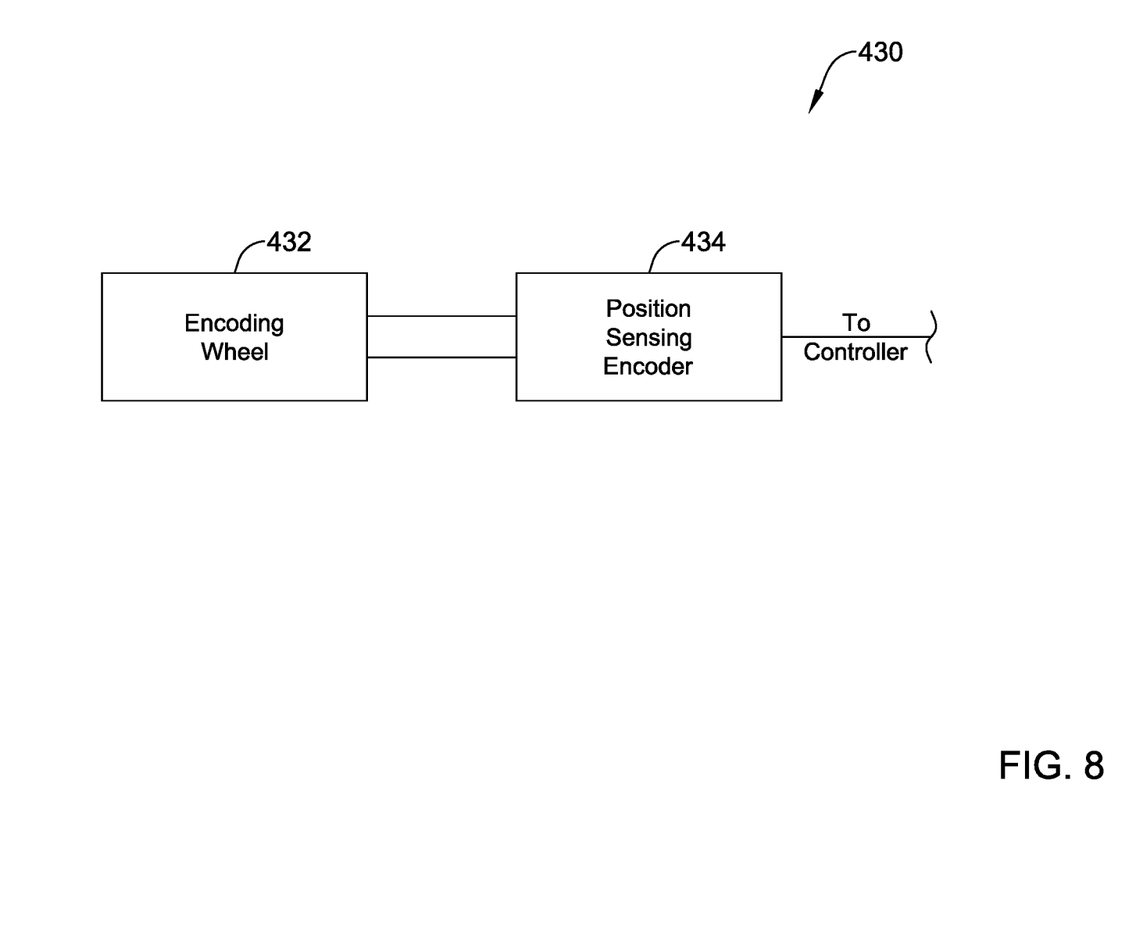
FIG. 8 is a schematic view of a guidewire motion detector usable in the example atherectomy system of FIG. 6.

It will be appreciated that motion of either the axial encoding wheel 422 or the radial encoding wheel 424, or both, needs to be communicated to the controller 410. FIG. 8 is a schematic view of a guidewire motion detector 430. The guidewire motion detector 430 includes an encoding wheel 432 that may, for example, represent either the axial encoding wheel 422 or the radial encoding wheel 424. A position sensing encoder 434 is operably coupled with the encoding wheel 432 such that the position sensing encoder 434 is able to detect when the encoding wheel 432 moves. In response to detecting movement of the encoding wheel 432, the position sensing encoder sends a communication informing the controller 410. The position sensing encoder 434 may take any form. The position sensing encoder 434 may be a mechanical encoder, for example.

Figure 9:
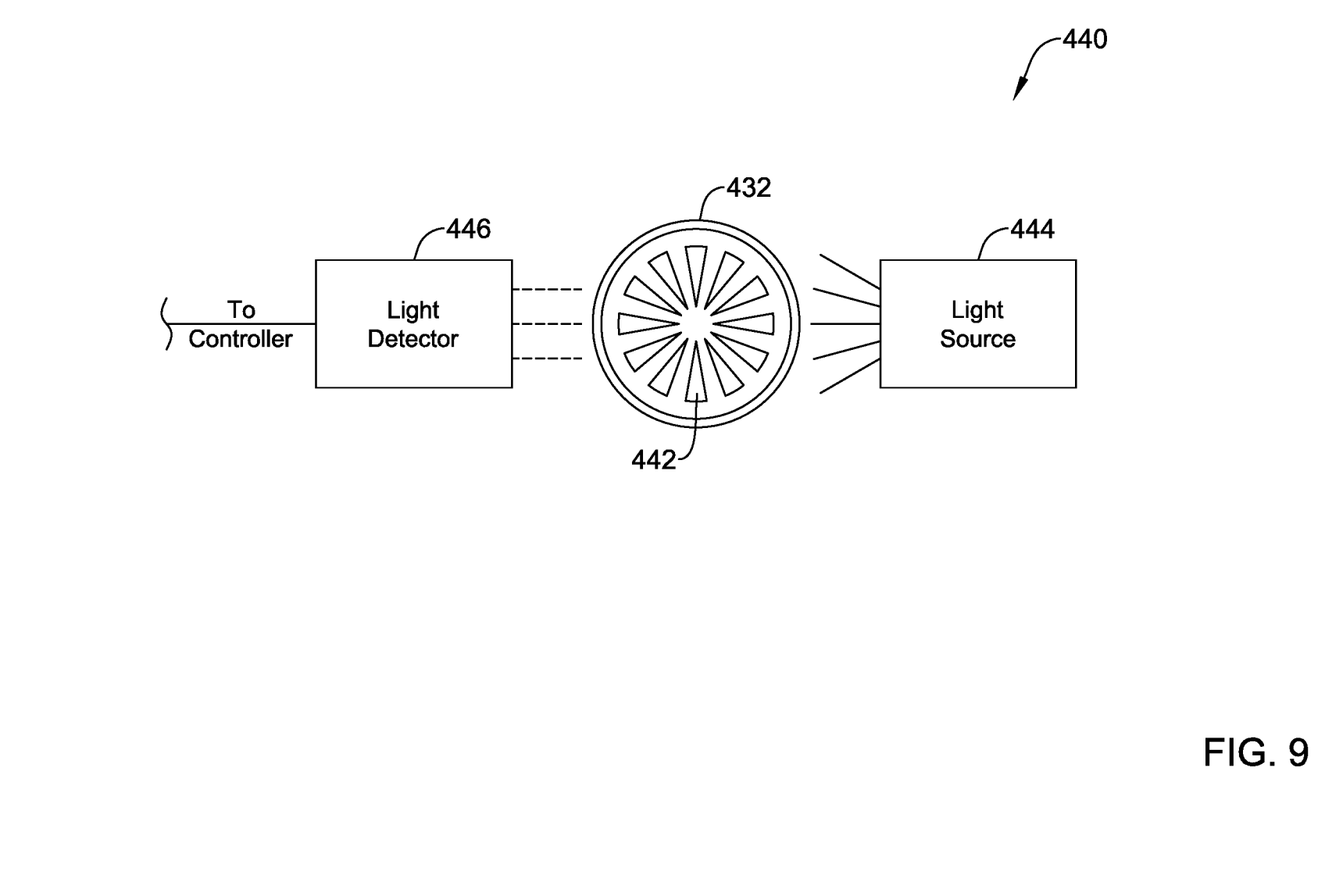
FIG. 9 is a schematic view of a guidewire motion detector usable in the example atherectomy system of FIG. 6.

In some cases, light may be used to detect movement of the encoding wheel 432. FIG. 9 is a schematic view of a guidewire motion detector 440 that includes the encoding wheel 432. As illustrated, the encoding wheel 432 includes a number of slots or apertures 442. Light may be emitted from a light source 444 and may impinge on the encoding wheel 432. The light source 444 may be an LED, a laser or a small incandescent bulb, for example. If the encoding wheel 432 is stationary, any light passing through the number of slots or apertures 442 will remain constant. However, if the encoding wheel 432 is rotating, the light passing through the number of slots or apertures 442 will change as the light either passes through a slot 442 or is blocked by the encoding wheel 432. A light detector 446 may be positioned to receive the light passing through the encoding wheel 432. The light detector 446 may, for example, be a photodiode, a phototransistor or a photocell. In response to detecting movement of the encoding wheel 432, the light detector 446 sends a communication informing the controller 410.

Figure 10:
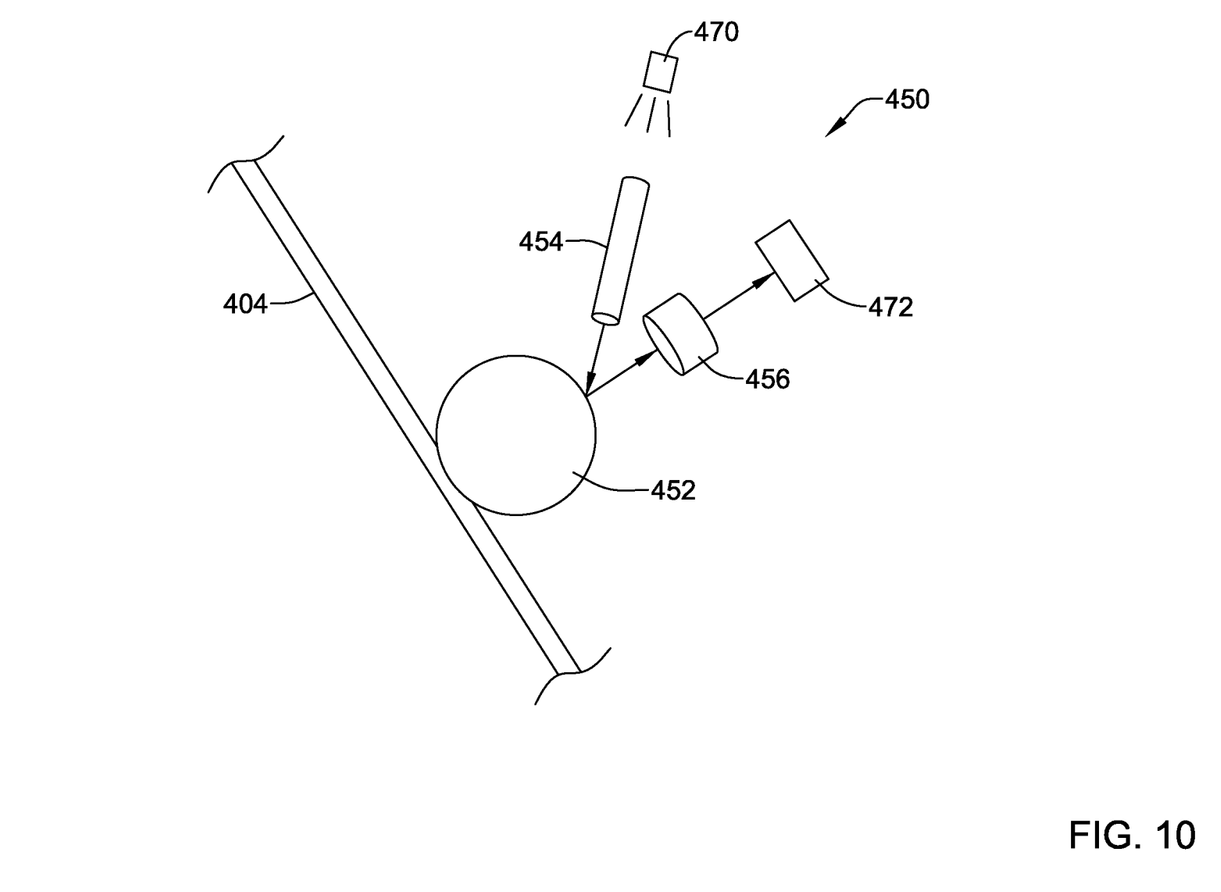
FIG. 10 is a schematic view of a guidewire motion detector usable in the example atherectomy system of FIG. 6.

FIG. 10 is a schematic view of a guidewire motion detector 450 that includes a track ball 452 that is positioned to contact the guidewire 404 such that any translation of the guidewire 404 or any rotation of the guidewire 404 causes the track ball to rotate. It will be appreciated that the track ball 452 is free to rotate in any direction. A light source 470 provides a light beam that impinges on the track ball 452. In some instances, as illustrated, the light beam may pass through an optical element 454 that is positioned between the light source 470 and the track ball 452. In some instances, the light source 470 may be a laser or a light emitting diode (LED). The optical element 454 may, for example, be a fiber optic element that enables flexibility in where the light source 470 may be located. As another example, the optical element 454 may be a focusing lens. In some cases, the track ball 452 may be a rubber ball, and may have a surface roughness sufficient that movement of the track ball 452 causes changes in how light is reflected by the track ball 452. The light reflected by the track ball 452 may pass through a lens 456 before impinging on a light detector 472. In some cases, the light detector 472 may be positioned to receive light from the light source 470 that is reflected by the surface of the track ball 452 and that passes through the lens 456. The light detector 472 may be an image processing chip that receives an image formed by the reflected light. In response to detecting movement of the track ball 452, the light detector 472 sends a communication informing the controller 410.

Figure 11:
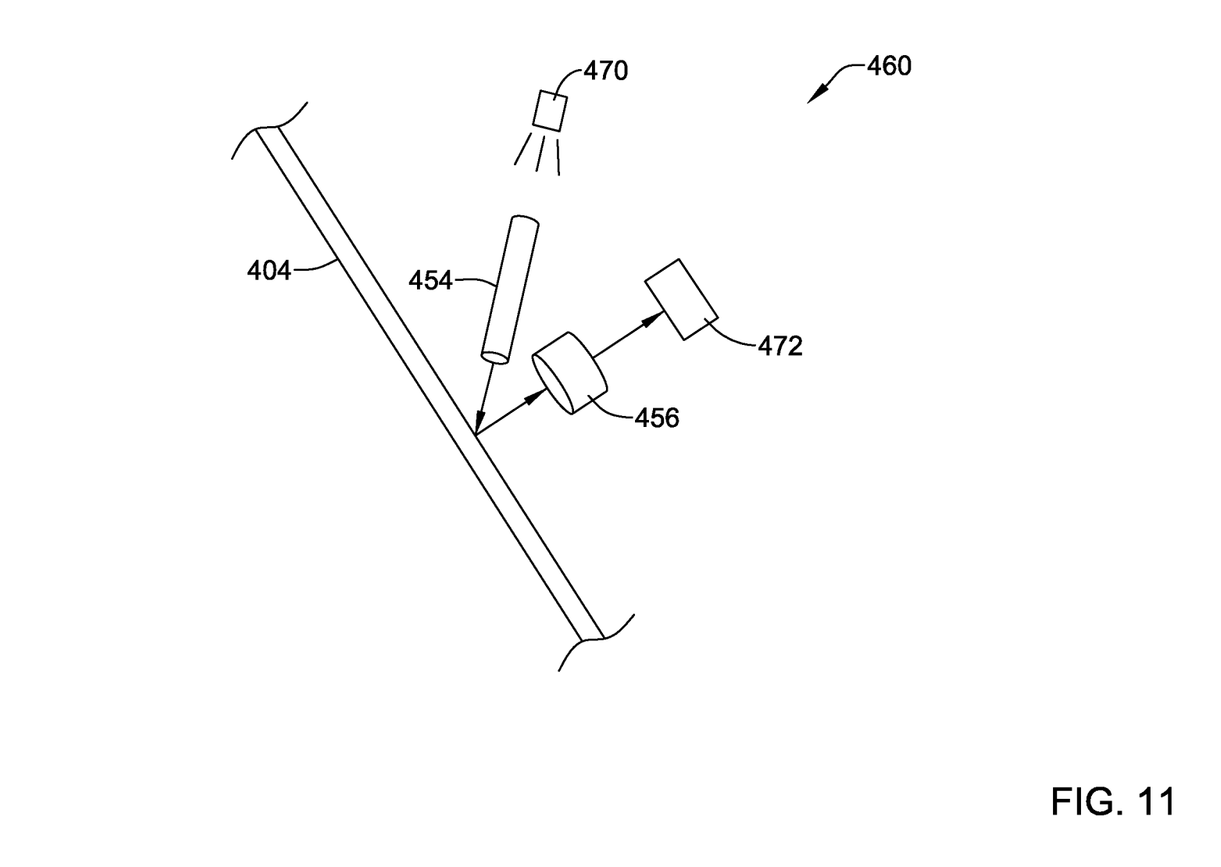
FIG. 11 is a schematic view of a guidewire motion detector usable in the example atherectomy system of FIG. 6.

FIG. 11 is a schematic view of a guidewire motion detector 460 that is configured to detect movement of the guidewire 404. The light source 454 provides a light beam that impinges on the guidewire 404. While not illustrated, in some cases the guidewire 404 may include a polymeric coating that provides the guidewire 404 with a roughness that is appropriate for the guidewire motion detector 460 to function, as in some cases, it is contemplated that the guidewire 404 may have a surface that is too smooth to function well with respect to detecting movement via changes in reflected light. Movement of the guidewire 404 may cause changes in how light is reflected by the guidewire 404. The light detector 472 may be positioned to receive light from the light source 470 that passes through the optical element 454 before being reflected by the surface of the guidewire 404 and then passes through the lens 456. As before, the optical element 454 may be a fiber optic cable, or the optical element 454 may be a focusing lens. In some instances, the light source 470 may be a laser or a light emitting diode (LED). In some cases, the light detector 472 may be a photodetector. The light detector 472 may be an optical detector. In some cases, fiber optics may be used to allow the light source 454 and/or the light detector 456 to be placed away from the guidewire 404, at a location that is perhaps more desirable from a packaging standpoint. In response to detecting movement of the guidewire 404, the light detector 472 sends a communication informing the controller 410.

Figure 12:
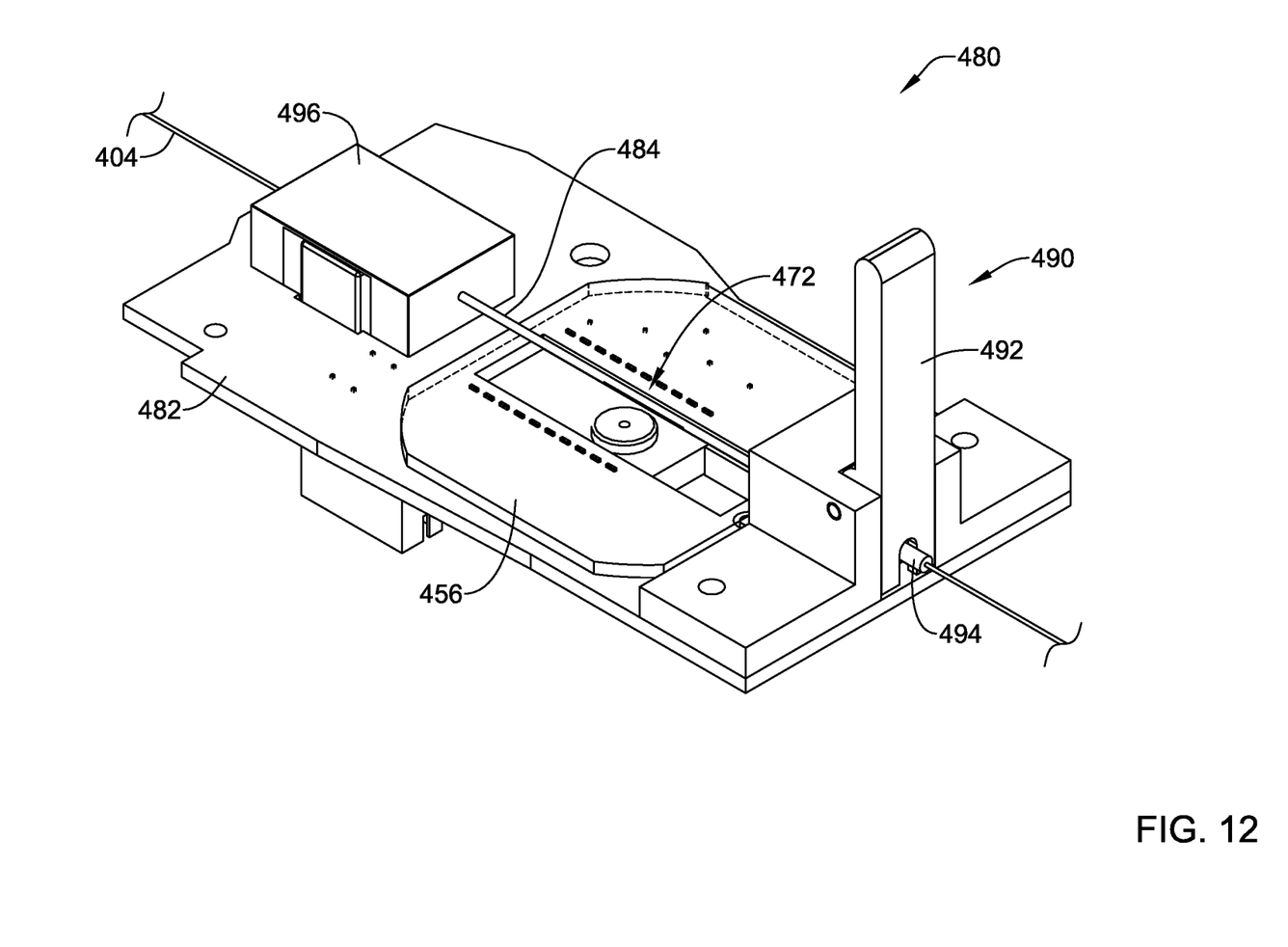
FIG. 12 is a perspective view of a guidewire motion detection assembly usable in the example atherectomy system of FIG. 6.

FIG. 12 is a perspective view of a guidewire motion detection assembly 480. As can be seen, the guidewire motion detection assembly 480 includes several components that are secured relative to a circuit board 482. The guidewire motion detection assembly 480 includes a wire brake 490 that can be actuated between a first position (illustrated) in which the guidewire 404 is locked in place and a second position in which the guidewire 404 is free to move relative to the guidewire motion detection assembly 480. The wire brake 490 includes a clamp lever 492 that is adapted to pivot relative to the circuit board 482 to either lock or unlock the guidewire 404. The wire brake 490 includes a clamp collet 494 that selectively engages the guidewire 404.

The lens 456, which is the same lens 456 referenced in FIGS. 10 and 11, is secured relative to the circuit board 482. As illustrated, the lens 456 is shown as being transparent in order to more easily see the light detector 472 secured to the circuit board 482. As shown, the light detector 472 is an image processing chip that is operably coupled to the controller 410 (FIG. 6) such that any detected motion of the guidewire 404 may be communicated to the controller 410. A guidewire presence detector 496 is secured relative to the circuit board 482 and may be considered as being an example of the guidewire presence detector 412 (FIG. 6).

In some cases, the guidewire motion detection assembly 480 may include a guidewire cover 484 that extends between the wire brake 490 and the guidewire presence detector 496. The guidewire cover 484 may be considered as providing a lumen for the guidewire 404 to easily extend through without running into any other components. In some cases, the guidewire cover 484 may include a slot that exposes the guidewire 404 to light. With respect to the guidewire motion detector 420 (FIG. 7) and the guidewire motion detector 430 (FIG. 8), the lens 456 and the light detector 472 shown in FIG. 12 may be omitted. With respect to the guidewire motion detector 450 (FIG. 10), it will be appreciated that the track ball 452 may be positioned to contact the guidewire 404 and such that the light emitted from the light source 470 reflects from the track ball 452 and is ultimately reflected to the light detector 472. In some cases, while not shown, the track ball 452 may be slightly spring-loaded in order to hold the track ball 452 in sufficient contact with the guidewire 404 such that movement of the guidewire 404 causes movement of the track ball 452. With respect to the guidewire motion detector 460 shown in FIG. 11, it will be appreciated that the light source 470 may be an LED or other light source (not shown) that is mounted to the circuit board 482.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:
1. An atherectomy system, comprising:
    an atherectomy burr;
    a drive mechanism adapted to rotatably actuate the atherectomy burr, the drive mechanism adapted to accommodate a guidewire extending therethrough;
    a guidewire extending through the drive mechanism;
    a guidewire presence detector configured to detect whether the guidewire is present;
    a guidewire motion detector adapted to detect movement of the guidewire when the guidewire is present; and a controller operably coupled to the guidewire motion detector and the guidewire presence detector, and the controller is adapted to regulate operation of the drive mechanism;

wherein the controller is further adapted to take action when the guidewire motion detector detects movement of the guidewire relative to the drive mechanism while the drive mechanism is operating;

wherein the controller is further adapted to prevent operation of the drive mechanism when the guidewire presence detector indicates a guidewire is not present.

2. The atherectomy system of claim 1, wherein the controller is further adapted to cease operation of the drive mechanism when the guidewire motion detector detects movement of the guidewire.

3. The atherectomy system of claim 1, wherein the controller is further adapted to provide an alarm when the guidewire motion detector detects movement of the guidewire.

4. The atherectomy system of claim 1, wherein the guidewire motion detector comprises an optical detector adapted to permit the guidewire to pass through the optical detector, wherein the presence of the guidewire is detected by the guidewire blocking at least some of the light passing through the optical detector.

5. The atherectomy system of claim 1, wherein the guidewire motion detector comprises an axial encoding wheel positioned in contact with the guidewire such that translation of the guidewire causes the axial encoding wheel to rotate.

6. The atherectomy system of claim 5, wherein the guidewire motion detector further comprises a position sensing encoder that is positioned to detect rotation of the axial encoding wheel and send an axial motion signal to the controller.

7. The atherectomy system of claim 5, wherein the axial encoding wheel comprises a plurality of slots extending through the axial encoding wheel and the guidewire motion detector further comprises an optical sensor sensitive to changes in light passing through the plurality of slots extending through the axial encoding wheel.

8. The atherectomy system of claim 1, wherein the guidewire motion detector comprises a radial encoding wheel positioned in contact with the guidewire such that rotation of the guidewire causes the radial encoding wheel to rotate.

9. The atherectomy system of claim 8, wherein the guidewire motion detector further comprises a position sensing encoder that is positioned to detect rotation of the radial encoding wheel and send a radial motion signal to the controller.

10. The atherectomy system of claim 8, wherein the radial encoding wheel comprises a plurality of slots extending through the radial encoding wheel and the guidewire motion detector further comprises an optical sensor sensitive to changes in light passing through the plurality of slots extending through the radial encoding wheel.

11. The atherectomy system of claim 1, wherein the guidewire motion detector comprises:

a light source positioned such that light from the light source impinges on the guidewire; and a light detector positioned such that light reflected from the guidewire contacts the light detector;

wherein changes in the light detected by the light detector indicates movement of the guidewire.

12. The atherectomy system of claim 1, further comprising a wire brake that facilitates insertion of the guidewire into the drive mechanism, the guidewire motion detector secured relative to the wire brake.

13. The atherectomy system of claim 1, wherein the drive mechanism comprises:

a drive cable coupled with the atherectomy burr; and a drive motor adapted to rotate the drive cable.

14. An atherectomy system, comprising:

an atherectomy burr;

a drive mechanism adapted to rotatably actuate the atherectomy burr, the drive mechanism adapted to accommodate a guidewire extending therethrough; a guidewire extending through the drive mechanism;

a guidewire presence detector configured to detect whether the guidewire is present;

a guidewire motion detector comprising:

a first encoding wheel positioned in contact with the guidewire such that translation of the guidewire relative to the drive mechanism causes the first encoding wheel to rotate;

a first position sensor adapted to detect rotation of the first encoding wheel and to output a translation movement signal;

a second encoding wheel positioned in contact with the guidewire such that rotation of the guidewire relative to the drive mechanism causes the second encoding wheel to rotate;

a second position sensor adapted to detect rotation of the second encoding wheel and to output a rotation movement signal;

a controller operably coupled to the guidewire presence detector and the guidewire motion detector, and the controller is adapted to regulate operation of the drive mechanism;

wherein the controller is further adapted to receive information indicating whether the guidewire is present, the translation movement signal, and/or the rotation movement signal and to take action when one or more of the following occurs: the information indicates the guidewire is not present, the translation movement signal indicates guidewire movement relative to the drive mechanism, or the rotation movement signal indicates guidewire movement relative to the drive mechanism;

wherein the controller is further adapted to prevent operation of the drive mechanism when the guidewire presence detector indicates a guidewire is not present.

15. The atherectomy system of claim 14, wherein taking action comprises providing an alarm.

16. The atherectomy system of claim 14, wherein the drive mechanism comprises:

a drive cable coupled with the atherectomy burr; and a drive motor adapted to rotate the drive cable.

* * * * *